United States Patent
Marchetti et al.

(10) Patent No.: US 10,292,931 B2
(45) Date of Patent: May 21, 2019

(54) STABLE LIQUID PHARMACEUTICAL COMPOSITION BASED ON TRAZODONE

(75) Inventors: Marcello Marchetti, Rome (IT);
Francesca Mariotti, Pesaro (IT);
Lorella Ragni, Chiaravalle (IT); Paolo Scarpetti, Falconara Marittima (IT);
Mauro Valenti, Magenta (IT)

(73) Assignee: AZIENDE CHIMICHE RIUNITE ANGELINI FRANCESCO A.C.R.A.F. S.p.A., Rome (IT)

(*) Notice: Subject to any disclaimer, the term of this patent is extended or adjusted under 35 U.S.C. 154(b) by 682 days.

(21) Appl. No.: 12/667,694

(22) PCT Filed: Jul. 22, 2008

(86) PCT No.: PCT/EP2008/059605
§ 371 (c)(1),
(2), (4) Date: May 18, 2010

(87) PCT Pub. No.: WO2009/016069
PCT Pub. Date: Feb. 5, 2009

(65) Prior Publication Data
US 2010/0256159 A1   Oct. 7, 2010

(30) Foreign Application Priority Data

Jul. 31, 2007 (IT) .............................. MI2007A1573

(51) Int. Cl.
| | |
|---|---|
| *A61K 31/496* | (2006.01) |
| *A61P 25/24* | (2006.01) |
| *A61K 9/00* | (2006.01) |
| *A61K 31/495* | (2006.01) |
| *A61K 47/10* | (2017.01) |

(52) U.S. Cl.
CPC ............ *A61K 9/006* (2013.01); *A61K 9/0019* (2013.01); *A61K 9/0095* (2013.01); *A61K 31/495* (2013.01); *A61K 31/496* (2013.01); *A61K 47/10* (2013.01)

(58) Field of Classification Search
CPC .... A61K 31/495; A61K 31/496; A61K 47/10; A61K 9/0019; A61K 9/006; A61K 9/0095
See application file for complete search history.

(56) References Cited

U.S. PATENT DOCUMENTS

| 4,154,832 A | 5/1979 | Silvestrini |
| 2008/0003275 A1 | 1/2008 | Vaisman |
| 2010/0056539 A1 | 3/2010 | Marchetti et al. |

FOREIGN PATENT DOCUMENTS

| IN | 2005MU01242 | * | 7/2007 |
| WO | 00 04875 | | 2/2000 |
| WO | 2005 004855 | | 1/2005 |
| WO | WO 2005/004855 | * | 1/2005 |

OTHER PUBLICATIONS

Henning (Polyethylene Glycols (PEGs) and the pharmaceutical industry, 2002).*
EDTA—2006 (DOW, Product Safety Assessment, Salts of Ethylenediaminetetracetic Acid (EDTA), Apr. 30, 2006, p. 1-5).*
Inactive Ingredients in Pharmaceutical Products (update), Pediatrics, 1997, 99, 268.*
Sundberg (Expert Opinion on Investigation Drugs, 2008).*
Polyglycols—Dow document (Synalox Lubricants, 2012).*
Excipient Development, 2006.*
U.S. Appl. No. 13/370,735, filed Feb. 10, 2012, Marchetti, et al.
Written Opinion issued in PCT/EP2008/059605.
U.S. Appl. No. 13/833,569, Mar. 15, 2013, Marchetti, et al.
U.S. Appl. No. 14/073,130, filed Nov. 6, 2013, Marchetti, et al.
U.S. Appl. No. 13/617,907, filed Sep. 14, 2012, Marchetti, et al.
Roussel, Hoechst Marion, "Molipaxin Liquid" URL:www.xpil.medicines.org.uk/fileserver.aspx?file=3078/current/resources/PIL.3078.2.pdf>, Total p. 1 (Nov. 2004) XP002510649 (Nov. 2004).
Combined Brazilian Office Action and Search Report dated Jul. 10, 2018 in Patent Application No. PI0814658-6 (with English translation of Categories of Cited Documents), citing documents AU and AX therein, 7 pages.
M. M. Al-Yassiri, et al. "Trazodone—A New Antidepressant" Life Sciences, vol. 28, No. 22, 1981, pp. 2449-2458.
"Ethyleneamines" The Dow Chemical Company, Aug. 2001, pp. 1-42.
Lanigan Rs, Yamarik TA. "Final Report on the Safety Assessment of EDTA, Calcium Disodium EDTA, Diammonium EDTA, Dipotassium EDTA, Disodium EDTA, TEA-EDTA, Tetrasodium EDTA, Tripotassium EDTA, Trisodium EDTA, HEDTA, and Trisodium HEDTA" International Journal of Toxicology, 21, Suppl 2, 2002, pp. 95-142.
Detpon Preechagoon, et al. "Formulation Development and Stability Testing of Oral Morphine Solution Utilizing Preformulation Approach" J Pharm Pharmaceut Sci (www.cspsCanada.org) 8 (2), 2005, pp. 362-369.

* cited by examiner

*Primary Examiner* — Umamaheswari Ramachandran
(74) *Attorney, Agent, or Firm* — Oblon, McClelland, Maier & Neustadt, L.L.P.

(57) ABSTRACT

A stable liquid pharmaceutical composition comprising an aqueous solution of a pharmaceutically acceptable salt of acid addition of trazodone, characterized in that said pharmaceutical composition has a pH value between 5.0 and 6.0, and comprises at least two cosolvents selected from the group comprising glycols and polyglycols.

15 Claims, No Drawings

STABLE LIQUID PHARMACEUTICAL COMPOSITION BASED ON TRAZODONE

CROSS REFERENCE TO RELATED APPLICATIONS

This application is 371 of International Patent Application No. PCT/EP2008/059605, filed on Jul. 22, 2008, and claims priority to Italian Patent Application No. MI 2007 A 001573, filed on Jul. 31, 2007.

FIELD OF THE INVENTION

The present invention relates to a stable liquid pharmaceutical composition based on trazodone.

In particular, the invention relates to a stable liquid pharmaceutical composition based on trazodone in which the pH ranges from 5.0 to 6.0.

PRIOR ART

Trazodone, or 2-[3-[4-(3-chlorophenyl)-1-piperazinylpropyl]-1,2,4-triazolo[4,3-a]pyridin-3(2)-one, is an antidepressant which, though having a significant effect on the serotonin receptors, is neither a psychostimulant, nor a MAO inhibitor, nor a tricyclic antidepressant. Furthermore, trazodone possesses analgesic properties.

Trazodone alleviates the characteristic symptoms of depression, in particular anxiety, somatization, psychomotor retardation, hypochondria, mood swings, irritability, insomnia, apathy, feeling of fatigue and lack of energy, depressed mood.

Trazodone has also proved effective in controlling pronounced essential tremor, probably on account of its serotoninergic activity.

Moreover, the antidepressant and anxiolytic properties of trazodone have proved useful in the treatment of symptoms of withdrawal from cocaine, benzodiazepines and alcohol.

Besides the above-mentioned activities, its sleep-inducing activity is also very interesting.

In the treatment of depression, trazodone is administered by the oral route as hydrochloride at initial doses of 100-150 mg per day, which can be increased by 50 mg every 3-4 days up to 300-400 mg per day. The daily dosage can be divided during the day to correspond to meal times or can be administered as a single dose at bedtime. In severe depression, up to 800 mg per day can be administered.

Trazodone is preferably used medically in the form of a pharmaceutically acceptable salt of acid addition, and more preferably in the form of the hydrochloride.

The solubility of trazodone hydrochloride at room temperature in the commonest solvents is as follows:

| | |
|---|---|
| water | 1.8 g/100 ml |
| 95% ethanol | 1.6 g/100 ml |
| methanol | 2.5 g/100 ml |
| chloroform | 3.6 g/100 ml |
| benzene | practically insoluble |
| ethyl ether | practically insoluble |
| octanol | less than 0.1 g/100 ml |
| olive oil | less than 0.1 g/100 ml |

The pH of a 1% (w/v) aqueous solution of trazodone hydrochloride is approx. 3.90.

In water, the solubility of trazodone hydrochloride increases with increase in acidity of the aqueous medium. However, as the acidity of the aqueous medium increases, the degradation of trazodone hydrochloride also increases.

This degradation appears to take place by an oxidative mechanism via the formation of an N-oxide, namely 4-(3-chlorophenyl)-1-[3-(3-oxa-2,3-dihydro-1,2,4-triazolo[4,3-α]pyridin-2-yl)-propyl]-piperazine $N^1$-oxide.

The oral pharmaceutical forms that are currently available commercially are either solid or liquid.

The solid pharmaceutical forms are also available as immediate-release or modified-release tablets.

The liquid pharmaceutical forms, for administration as oral drops, have the advantage that they permit greater modularity and personalization of the therapeutic dose.

Various liquid formulations, for oral use (drops, syrup) or parenteral use (vials for injection), with concentrations of trazodone hydrochloride equal to approx. 1% (w/v), are being marketed. A liquid pharmaceutical composition for oral use that is widely used at present has a maximum concentration of trazodone hydrochloride of 2.5% (w/v), it contains ethanol and glycerol as cosolvents, and its pH is in the range from 4.3 to 4.7.

However, this liquid pharmaceutical composition has certain disadvantages.

A first disadvantage is the low concentration of trazodone, so that the therapeutic dosages required involve counting a large number of drops.

A second disadvantage is that trazodone is incompatible with the consumption of ethanol. Therefore it would be preferable to avoid the use of ethanol as cosolvent, even if the amount taken by the patient with the aforesaid liquid pharmaceutical composition for oral use is at present almost negligible.

A third disadvantage is that its physical appearance changes over time, with the solution turning yellow, owing to the formation, primarily by an oxidative mechanism, of degradation products of trazodone hydrochloride.

Therefore there is still a great need for a liquid pharmaceutical composition of trazodone hydrochloride for oral administration in which an amount of trazodone hydrochloride greater than or equal to 1% (w/v) can be dissolved stably, does not contain ethanol as solvent or cosolvent, and does not turn yellow over time.

DEFINITIONS

In the present description and in the claims, the expression "stable composition" means a solution of trazodone hydrochloride that does not give rise to a precipitate after 30 days of storage at a temperature of 4° C. and in which the individual degradation products of trazodone hydrochloride do not exceed 0.2% after 3 months at 40° C.

DESCRIPTION OF THE INVENTION

It was found, surprisingly, that this aim is achieved with a liquid pharmaceutical composition comprising an aqueous solution of a pharmaceutically acceptable salt of acid addition of trazodone in which the pH value is between 5.0 and 6.0 and which contains at least two cosolvents selected from the group comprising glycols and polyglycols.

Preferably, the salt of acid addition of trazodone is the hydrochloride.

Preferably, the pH value is between 5.0 and 5.5.

The concentration of trazodone hydrochloride in said liquid pharmaceutical composition is preferably between 1% and 15% (w/v), more preferably between 3% and 10% (w/v), and even more preferably between 4% and 8% (w/v).

Advantageously, the concentration of trazodone hydrochloride in said liquid pharmaceutical composition is approx. 6% (w/v).

Surprisingly, it was found that the use of at least two cosolvents selected from the group comprising glycols and polyglycols makes it possible to obtain a stable liquid composition of trazodone hydrochloride at concentrations above 3% (w/v), and preferably even above 6% (w/v).

The solubility of trazodone hydrochloride in the presence of mixtures of cosolvents according to the present invention can reach concentration levels of the order of 10-15%.

Generally, the total amount of cosolvents according to the present invention is in the range from 20 to 90% (w/v). Preferably, said total amount is in the range from 30 to 85% (w/v) and, more preferably, from 40 to 80% (w/v), Preferably, the liquid pharmaceutical composition of trazodone hydrochloride of the present invention comprises two cosolvents, each independently in an amount in the range from 5% to 50% (w/v), preferably from 15% to 45% (w/v).

Alternatively, the liquid pharmaceutical composition of trazodone hydrochloride of the present invention comprises three cosolvents, each independently in an amount in the range from 5% to 40% (w/v), preferably from 10% to 30% (w/v).

The effect of the mixture of two or more cosolvents according to the present invention is all the more surprising if we bear in mind that, as already mentioned, the solubility of trazodone hydrochloride decreases with decrease in acidity of the aqueous medium. Thus, the possibility of increasing the concentration of trazodone hydrochloride from 2.5% to 6% (w/v), with change from pH 4.3-4.7 to pH 5.0-5.5, was completely unexpected. The increase is in fact 140%.

Moreover, the effect of the mixture of two or more cosolvents according to the present invention is even more surprising in view of the fact that none of the cosolvents tested alone was able to provide a stable composition of trazodone hydrochloride at 6% (w/v). Thus, the combination of two or more cosolvents had an unexpected synergistic effect on the solubility of trazodone hydrochloride.

Generally, the liquid pharmaceutical composition of trazodone hydrochloride according to the present invention is administered by the oral route, but it can also be administered by other routes, for example parenterally.

The liquid pharmaceutical composition of trazodone hydrochloride according to the present invention can be prepared in various pharmaceutical forms, such as, for example in the form of aqueous solution for administration as drops, in the form of syrup, or in the form of aqueous solution for injectable vials.

Typically, the liquid pharmaceutical composition of trazodone hydrochloride of the present invention is dispensed in the form of drops.

In a preferred embodiment of the present invention the pH is between 5.0 and 5.5.

A typical example of a glycol used advantageously in the present invention is propylene glycol.

Typical examples of polyglycols preferably used in the present invention are: polyethylene glycol 200 (PEG 200), polyethylene glycol 300 (PEG 300), polyethylene glycol 400 (PEG 400), polyethylene glycol 600 (PEG 600), polyethylene glycol 1000 (PEG 1000), polyethylene glycol 1500 (PEG 1500), polyethylene glycol 3000 (PEG 3000), polyethylene glycol 3350 (PEG 3350), polyethylene glycol 4000 (PEG 4000), and polyethylene glycol 6000 (PEG 6000).

Typical examples of mixtures of glycols and polyglycols according to the present invention are: propylene glycol+ PEG 200, propylene glycol +PEG 400, propylene glycol+ PEG 6000, propylene glycol+PEG 200+PEG 6000, propylene glycol+PEG 400+PEG 6000, PEG 200+PEG 6000, and PEG 400+PEG 6000.

Advantageously, the liquid pharmaceutical composition of trazodone hydrochloride of the present invention comprises an antioxidant for preventing oxidative degradation of trazodone, regarded as the main cause of yellowing of the known solutions.

Advantageously, the antioxidant is selected from the group comprising vitamin C and its salts, vitamin E, gallic acid and its derivatives, such as propyl gallate, malic acid, sulphite of sodium or of potassium, bisulphite of sodium or of potassium, metabisulphite of sodium or of potassium, butylated hydroxyanisole (BHA), and butylated hydroxytoluene (BHT). Preferably, the antioxidant is selected from the group comprising gallic acid and its derivatives.

Preferably, the liquid pharmaceutical composition of trazodone hydrochloride of the present invention also comprises other ingredients commonly used in the preparation of pharmaceutical formulations, such as, for example, chelating agents, buffers, pH correctors, surfactants, cyclodextrins, colorants, sweeteners, preservatives and the like.

Preferably, the chelating agent is selected from the group comprising ethylenediamine tetraacetic acid (EDTA) and its salts, such as, for example, dipotassium ethylenediamine tetraacetate, calcium disodium ethylenediamine tetraacetate, tetrasodium ethylenediamine tetraacetate, trisodium ethylenediamine tetraacetate.

The liquid pharmaceutical composition of the present invention is prepared by conventional techniques that comprise dissolution, mixing, filtration and the like.

Advantageously, the liquid pharmaceutical composition of the present invention is prepared in a nitrogen gas atmosphere by bubbling gaseous nitrogen in the solution under preparation.

The following examples will illustrate the invention, though without limiting it.

EXAMPLE 1

Comparative

Drops

| | |
|---|---|
| A. Trazodone hydrochloride | 6 g |
| B. Propylene glycol | 40 g |
| C. Purified water | qsf. 100 ml |

B and 90% of C were put in a 250-ml beaker and the solution was heated to 50° C. with magnetic stirring at a speed of 500 rev/min.

When the solution reached 50° C., A and the remainder of C were added, still with magnetic stirring at 500 rev/min, After such additions, the pH was corrected from 3.38 to 5.20 with approx. 18 g of 1% NaOH aqueous solution.

The solution was then cooled to 25° C., maintaining constant magnetic stirring at a speed of 500 rev/min.

EXAMPLE 2

Comparative

The procedure of Example 1 was repeated, replacing the propylene glycol with an equal amount of PEG 400.

EXAMPLE 3

Invention

Drops

| | |
|---|---:|
| A. Trazodone hydrochloride | 6 g |
| B. Propylene glycol | 20 g |
| C. PEG 400 | 30 g |
| D. Purified water | qsf. 100 ml |

B, C and 90% of D were put in a 250-ml beaker and the solution was heated to 50° C. with magnetic stirring at a speed of 500 rev/min.

When the solution reached 50° C., A and the remainder of D were added, still with magnetic stirring at 500 rev/min.

After addition, the pH was corrected from 4.50 to 5.20 with approx. 18 g of 1% NaOH aqueous solution.

The solution was then cooled to 25° C., maintaining constant magnetic stirring at a speed of 500 rev/min.

EXAMPLE 4

Invention

Drops

| | |
|---|---:|
| A. Trazodone hydrochloride | 6 g |
| B. Propylene glycol | 30 g |
| C. PEG 400 | 35 g |
| D. Sodium metabisulphite | 0.1 g |
| E. Disodium EDTA | 0.1 g |
| F. Purified water | qsf. 100 ml |

D and E were put in a 250-ml beaker and were dissolved at 25° C., with magnetic stirring at a speed of 500 rev/min, in 50% of F.

Then, still at 25° C. and with magnetic stirring at a speed of 500 rev/min, B, C and 45% of F were added.

Finally, still at 25° C. and with magnetic stirring at a speed of 500 rev/min, A and the remaining 5% of F were added and the pH was corrected from 4.80 to 5.20 with approx. 15 g of 1% NaOH aqueous solution.

EXAMPLE 5

Invention

Drops

| | |
|---|---:|
| A. Trazodone hydrochloride | 6 g |
| B. Propylene glycol | 30 g |
| C. PEG 400 | 35 g |
| D. Propyl gallate | 0.1 g |
| E. Disodium EDTA | 0.1 g |
| F. Purified water | qsf. 100 ml |

D was put in a 250-ml beaker and was dissolved at 25° C. and with magnetic stirring at a speed of 500 rev/min in B.

E was dissolved at 25° C. with magnetic stirring at a speed of 500 rev/min in 50% of F.

The two solutions were combined, and C and 45% of F were added, at 25° C. and with magnetic stirring at a speed of 400-500 rev/min.

Finally, A and the remaining 5% of F were added, at 25° C. and with magnetic stirring at a speed of 500 rev/min, and the pH was adjusted from 4.66 to 5.20 with 15 g of 1% NaOH aqueous solution.

EXAMPLE 6

Invention

Drops

| | |
|---|---:|
| A. Trazodone hydrochloride | 6 g |
| B. Propylene glycol | 40 g |
| C. PEG 6000 | 5 g |
| D. Propyl gallate | 0.1 g |
| E. Disodium EDTA | 0.1 g |
| F. Purified water | qsf. 100 ml |

D was put in a 250-ml beaker and was dissolved at 25° C. and with magnetic stirring at a speed of 500 rev/min in B and C.

E was dissolved separately, at 25° C. and with magnetic stirring at a speed of 500 rev/min, in 50% of F.

The two solutions were combined, and 45% of F was added, at 25° C. and with magnetic stirring at a speed of 500 rev/min.

Finally, A and the remaining 5% of F were added, at 25° C. and with magnetic stirring at a speed of 500 rev/min, and the pH was adjusted from 4.25 to 5.20 with approx. 18 g of 1% NaOH aqueous solution.

EXAMPLE 7

Invention

Drops

| | |
|---|---:|
| A. Trazodone hydrochloride | 6 g |
| B. Propylene glycol | 30 g |
| C. PEG 400 | 35 g |
| D. Propyl gallate | 0.1 g |
| E. Disodium EDTA | 0.1 g |
| F. Sucralose | 0.05 g |
| G. Purified water | qsf. 100 ml |

D was put in a dissolver equipped with a turbine agitator and was dissolved at room temperature in B.

E was dissolved separately, at 25° C. and with magnetic stirring at a speed of 500 rev/min, in 50% of G.

The two solutions were combined, and C, F and 45% of G were added, at 25° C. and with magnetic stirring at a speed of 400-500 rev/min.

Finally, A and the remaining 5% of G were added, at 25° C. and with magnetic stirring at a speed of 500 rev/min, and the pH was adjusted from 4.61 to 5.20 with approx. 18 g of 1% NaOH aqueous solution.

EXAMPLE 8

Invention

Syrup

| | |
|---|---|
| A. Trazodone hydrochloride | 1 g |
| B. PEG 400 | 20 g |
| C. Propylene glycol | 10 g |
| D. PEG 6000 | 10 g |
| E. Sodium saccharin | 0.08 g |
| F. Aroma | 0.1 g |
| G. Benzoic acid | 0.1 g |
| H. Purified water | qsf. 100 ml |

B, C and D were put in a 250-ml beaker and were dissolved at 25° C. and with magnetic stirring at a speed of 500 rev/min in 60% of H. Then, still at 25° C. and with magnetic stirring at a speed of 500 rev/min, A was added.

G was dissolved separately, at 25° C. and with magnetic stirring at a speed of 500 rev/min, in 40% of H.

The two solutions were combined, and E and F were added, still at a temperature of 25° C. and with magnetic stirring at a speed of 500 rev/min.

Then the pH was corrected from 4.35 to 5.40 with approx. 1 g of 10% NaOH aqueous solution.

EXAMPLE 9

Invention

Aqueous Solution for Injectable Vials

| | |
|---|---|
| A. Trazodone hydrochloride | 1 g |
| B. PEG 400 | 30 g |
| C. Propylene glycol | 10 g |
| D. Purified water | qsf. 100 ml |

B and C were put in a 250-ml beaker and were dissolved at 25° C. with magnetic stirring at a speed of 500 rev/min in 90% of D. Then, still at 25° C. and with magnetic stirring at a speed of 500 rev/min, A was added, stirring until it had dissolved completely.

Finally, the remaining 10% of D was added and the pH was corrected from 4.60 to 5.20 with approx. 1 g of 10% NaOH aqueous solution.

EXAMPLE 10

Invention

Drops

| | |
|---|---|
| A. Trazodone hydrochloride | 6 g |
| B. PEG 400 | 35 g |
| C. Propylene glycol | 30 g |
| D. Disodium EDTA | 0.1 g |
| E. Sucralose | 0.15 g |
| F. Anhydrous citric acid | 0.5 g |
| G. Propyl gallate | 0.1 g |
| H. Purified water | qsf. 100 ml |

G was put in a 250-ml beaker and was dissolved at 25° C. with magnetic stirring at a speed of 500 rev/min in C.

D was dissolved separately in a 150-ml beaker, at 25° C. and with magnetic stirring at a speed of 300-400 rev/min, in 50% of H.

The two solutions were combined, and A, B, E and F were added, still at 25° C. and with magnetic stirring at a speed of 500 rev/min.

Finally, the remaining 50% of H was added and the pH was corrected from 4.80 to 5.20 with approx. 15 g of 1% NaOH aqueous solution.

EXAMPLE 11

Stability Tests

The formulations in examples 1 to 10 were stored at room temperature for 30 days and in a refrigerator at 4° C. for 30 days. All the formulations proved to be stable in storage at room temperature, remaining clear and free from precipitate. Formulations 1 and 2 produced a precipitate when stored in the refrigerator at 4° C. Formulations 3 to 10 also remained stable on storage in the refrigerator, remaining clear and free from precipitate. The formulation of Example 3 was additionally stored in the refrigerator at 4° C. for 4 months, and did not display formation of precipitate.

The formulations of examples 3, 5, 6 and 7 were stored at 40° C. and 75% relative humidity, for a variable length of time as shown in Tables 1 and 2 below.

At the end of each period of storage, the formulations were submitted to pharmaceutical analyses, to verify their appearance and presence of any precipitate, and chemical analyses, for verifying presence of trazodone degradation products. The results are presented in the same Tables 1 and 2.

TABLE 1

| | Pharmaceutical analyses | | | |
|---|---|---|---|---|
| | Storage at 40° C. and 75% RH for: | | | |
| | 1 month | 2 months | 3 months | 4 months |
| Example 3 | — | Solution slightly yellowed No precipitate pH 5.10 | Solution slightly yellowed No precipitate | Solution yellowed pH 5.04 |
| Example 5 | — | Clear, colourless solution No precipitate | — | Clear, colourless solution No precipitate |
| Example 6 | Clear, colourless solution No precipitate | — | — | — |
| Example 7 | Clear, colourless solution No precipitate pH 5.27 | — | Clear, colourless solution No precipitate pH 5.10 | — |

TABLE 2

| | Chemical analyses | | | |
|---|---|---|---|---|
| | Storage at 40° C. and 75% RH for: | | | |
| | 1 month | 2 months | 3 months | 4 months |
| Example 3 | — | — | N-oxide 0.11% Others 0.09% | — |

TABLE 2-continued

Chemical analyses

Storage at 40° C. and 75% RH for:

| | 1 month | 2 months | 3 months | 4 months |
|---|---|---|---|---|
| Example 5 | N-oxide 0.05%<br>Others 0.01% | N-oxide 0.05%<br>Others 0.01% | — | N-oxide 0.05%<br>Others 0.02% |
| Example 7 | N-oxide 0.03%<br>Others <0.02% | — | N-oxide 0.04%<br>Others <0.02% | |

The invention claimed is:

1. A liquid pharmaceutical composition, comprising:
 (a) water;
 (b) 6 to 8% w/v of trazodone hydrochloride;
 (c) propylene glycol; and
 (d) one or more cosolvents selected from the group consisting of polyethylene glycol 200, polyethylene glycol 300, polyethylene glycol 400, polyethylene glycol 600, polyethylene glycol 1000, polyethylene glycol 1500, polyethylene glycol 3000; polyethylene glycol 3350, polyethylene glycol 4000, and polyethylene glycol 6000,
 wherein said liquid pharmaceutical composition is a solution and has a pH value of from 5.0 to 6.0, and said propylene glycol and said one or more cosolvents are present in a total amount of 45 to 90% w/v.

2. The liquid pharmaceutical composition according to claim 1, which has a pH value of from 5.0 to 5.5.

3. The liquid pharmaceutical composition according to claim 1, which comprises said one or more cosolvents in a total amount of from 45% to 85% (w/v).

4. The liquid pharmaceutical composition according to claim 3, which comprises said one or more cosolvents in a total amount of from 45% to 80% (w/v).

5. The liquid pharmaceutical composition according to claim 1, which comprises two cosolvents, each independently in an amount of from 5% to 50% (w/v), and in total amount not greater than 90% (w/v).

6. The liquid pharmaceutical composition according to claim 1, which comprises three cosolvents, each independently in an amount of from 5% to 40% (w/v), and in total amount not greater than 90% (w/v).

7. The liquid pharmaceutical composition according claim 1, which comprises said trazodone hydrochloride in an amount of about 6% (w/v).

8. The liquid pharmaceutical composition according to claim 1, wherein (c) and (d), together, is a combination which is selected from the group consisting of
 propylene glycol+PEG 200,
 propylene glycol+PEG 400,
 propylene glycol+PEG 6000,
 propylene glycol+PEG 200+PEG 6000, and
 propylene glycol+PEG 400+PEG 6000.

9. The liquid pharmaceutical composition according to claim 1, further comprising at least one antioxidant.

10. The liquid pharmaceutical composition according to claim 9, wherein said at least one antioxidant is selected from the group consisting of vitamin C, a salt of vitamin C, vitamin E, gallic acid, inalic acid, sodium sulphite, potassium sulphite, sodium bisulphite, potassium bisulphite, sodium metabisulphite, potassium metabisulphite, butylated hydroxyanisole, and butylated hydroxytoluene.

11. The liquid pharmaceutical composition according to claim 1, further comprising at least one additive selected from the group consisting of a chelating agent, a buffer, a pH corrector, a surfactant, a cyclodextrin, a colorant, a sweetener, and a preservative.

12. The liquid pharmaceutical composition according to claim 11, wherein said chelating agent is selected from the group consisting of ethylenediamine tetraacetic acid, sodium ethylenediamine tetraacetic acid, potassium ethylenediamine tetraacetic acid, and calcium ethylenediamine tetraacetic acid.

13. The liquid pharmaceutical composition according to claim 1, wherein (d) is one or two cosolvents wherein said cosolvents are selected from the group consisting of polyethylene glycol 200, polyethylene glycol 300, polyethylene glycol 400, polyethylene glycol 600, polyethylene glycol 1000, polyethylene glycol 1500, polyethylene glycol 3000; polyethylene glycol 3350, polyethylene glycol 4000, and polyethylene glycol 6000.

14. A liquid pharmaceutical composition, consisting of:
 (a) water;
 (b) 6 to 8% w/v of trazodone hydrochloride;
 (c) propylene glycol;
 (d) one or more cosolvents selected from the group consisting of polyethylene glycol 200, polyethylene glycol 300, polyethylene glycol 400, polyethylene glycol 600, polyethylene glycol 1000, polyethylene glycol 1500, polyethylene glycol 3000; polyethylene glycol 3350, polyethylene glycol 4000, and polyethylene glycol 6000, and
 (e) at least one additive selected from the group consisting of an antioxidant, a chelating agent, a buffer, a pH corrector, a surfactant, a cyclodextrin, a colorant, a sweetener, and a preservative;
 wherein said liquid pharmaceutical composition is a solution and has a pH value of from 5.0 to 6.0, and said propylene glycol and said one or more cosolvents are present in a total amount of 45 to 90% w/v.

15. The liquid pharmaceutical composition according to claim 14, wherein (c) and (d), together, is a combination which is selected from the group consisting of
 propylene glycol+PEG 200,
 propylene glycol+PEG 400,
 propylene glycol+PEG 6000,
 propylene glycol+PEG 200+PEG 6000, and
 propylene glycol+PEG 400+PEG 6000.

* * * * *